United States Patent [19]

Enloe

[11] Patent Number: 4,895,568

[45] Date of Patent: Jan. 23, 1990

[54] DIAPER LINER WITH SELECTIVELY ELASTICIZED PORTIONS

[75] Inventor: Kenneth M. Enloe, Neenah, Wis.

[73] Assignee: Kimberly-Clark Corporation, Neenah, Wis.

[21] Appl. No.: 234,786

[22] Filed: Aug. 18, 1988

[51] Int. Cl.[4] .......................................... A61F 13/16
[52] U.S. Cl. ............................... 604/385.2; 604/385.1
[58] Field of Search ................ 604/385.1, 385.2, 378, 604/369

[56] References Cited

U.S. PATENT DOCUMENTS

| | | | |
|---|---|---|---|
| 2,866,459 | 12/1958 | Sobelson | 128/284 |
| 3,339,548 | 9/1967 | Seltzer | 128/284 |
| 3,885,568 | 5/1975 | Schaar | 604/385.1 |
| 3,926,189 | 12/1975 | Taylor | 604/385.1 |
| 3,995,637 | 12/1976 | Schaar | 128/287 |
| 4,023,571 | 5/1977 | Comerford et al. | 128/290 |
| 4,029,100 | 6/1977 | Karami | 604/369 |
| 4,050,462 | 9/1977 | Woon et al. | 128/287 |
| 4,300,562 | 11/1981 | Pieniak | 128/287 |
| 4,323,070 | 4/1982 | Ternstrom et al. | 128/287 |
| 4,326,528 | 4/1982 | Ryan et al. | 604/385.2 |
| 4,381,782 | 5/1983 | Mazurak et al. | 604/368 |
| 4,433,972 | 2/1984 | Malfitano | 604/385.1 |
| 4,501,587 | 2/1985 | Enloe | 604/385.1 |
| 4,559,051 | 12/1985 | Hanson | 604/385.1 |
| 4,578,073 | 3/1986 | Dysart et al. | 604/397 |
| 4,662,877 | 5/1987 | Williams | 604/385 |
| 4,681,577 | 7/1987 | Stern et al. | 604/378 |
| 4,704,116 | 11/1987 | Enloe | 604/385 |
| 4,738,677 | 4/1988 | Foreman | 604/385 |
| 4,795,451 | 1/1989 | Buckley | 604/385.2 |
| 4,828,555 | 5/1989 | Hermansson | 604/379 |

FOREIGN PATENT DOCUMENTS

EP0183668A2  6/1986  European Pat. Off. .
1489626  7/1967  France ................................ 604/378

Primary Examiner—C. Fred Rosenbaum
Assistant Examiner—Mark O. Polatta
Attorney, Agent, or Firm—Paul Yee

[57] ABSTRACT

A distinctive absorbent article includes a backsheet layer, a substantially liquid-permeable liner layer, and an absorbent body located between the backsheet and liner layers. The backsheet and liner layers generally define a front waistband section, a rear waistband section and an intermediate section of the article, with the intermediate section interconnecting the front and rear waistband sections. A resilient barrier member is located in the intermediate section of the article, and includes at least a portion which extends generally transversely along the article cross-direction. The barrier member extends toward the body of the wearer and operably inhibits the longitudinal movement of liquid or viscous waste materials between the front and rear waistband sections of the article.

15 Claims, 4 Drawing Sheets

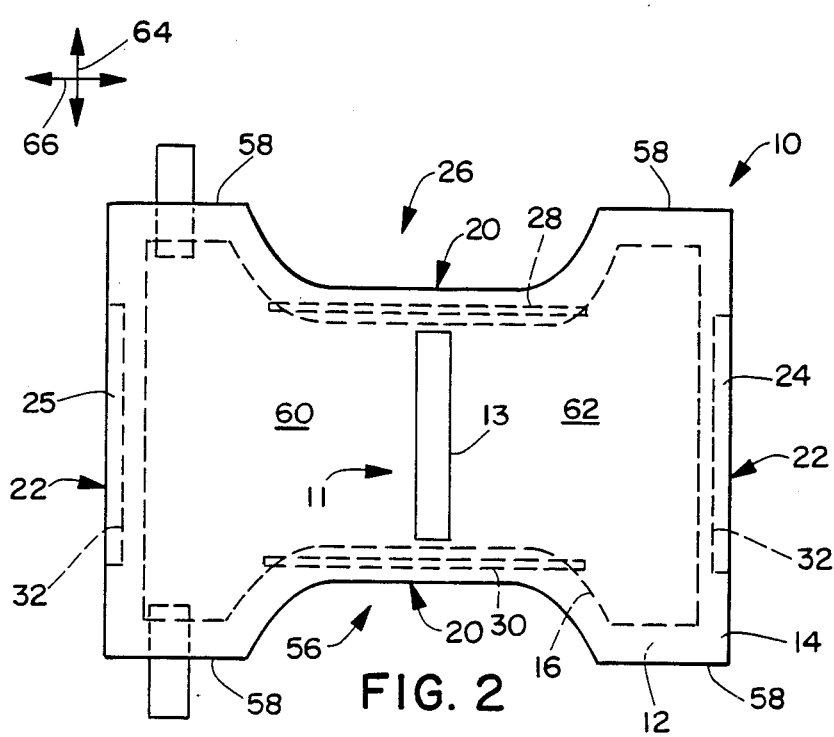
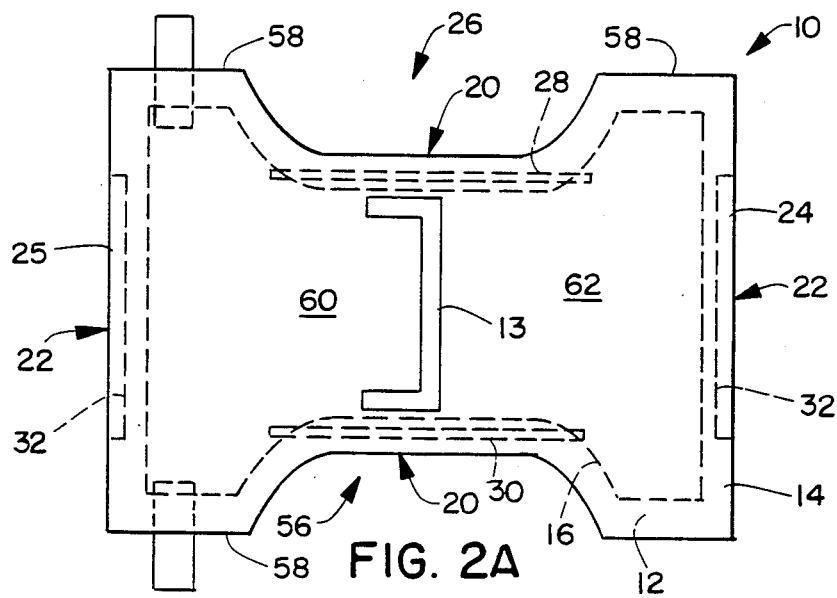

DIAPER LINER WITH SELECTIVELY ELASTICIZED PORTIONS

FIELD OF THE INVENTION

The present invention pertains to an absorbent article constructed and arranged for positioning adjacent the body of a wearer. More particularly, the present invention relates to an absorbent article having a resilient barrier section which inhibits the movement of liquid or viscous waste materials along the longitudinal dimension of the article.

BACKGROUND OF THE INVENTION

Conventional absorbent articles, such as disposable diapers, have employed elastic members to produce stretchable gathers along the margins of the article. For example, U.S. Pat. No. 4,050,462 issued Sept. 27, 1977 to L. Woon et al. describes a disposable diaper having elasticized side margins which are configured for placement around the legs of a wearer. U.S. Pat. No. 4,300,562 issued Nov. 17, 1981 to H. Pieniak describes an absorbent article having elasticized side margins and also elasticized waistband margins.

U.S. Pat. No. 4,662,877 issued May 5, 1987 to F. Williams describes a disposable diaper comprising a moisture-impermeable backing sheet, a fibrous absorbent batt, and a flexible hydrophobic facing sheet overlying the batt. The facing sheet has an aperture in the central crotch region of the diaper with zones of elastication in the facing sheet tending to apply tensioning forces to the facing sheet for urging the facing sheet (at least in the regions adjacent the aperture) away from the underlying batt structure.

European patent application Ser. No. EP 0 183 668 A2 published for 04 Jun., 1986 with the inventor listed as L. Widlund describes a disposable diaper comprising a liquid-permeable first outer layer, and a preferably liquid-impermeable second outer layer applied to either side of an absorbent body. Partly elastic members applied under tension are intended for bringing the edge portions of the article into tightly sealing contact with the body of the wearer. The primary distinguishing feature of the article is that the elastic members are comprised in a network. In particular, elastic members extend transversely across the width of the diaper.

U.S. Pat. No. 2,866,459 describes a diaper having longitudinal elastic stitching at the two longitudinal sides of the diaper and parallel transverse elastic stitching across the width of the diaper.

U.S. Pat. No. 3,339,548 issued Sept. 5, 1967 to N. Seltzer describes a diaper which has been contoured to form concavely configured opposite side edges.

U.S. Pat. No. 3,995,637 issued Dec. 7, 1976 to C. Schaar describes a disposable diaper comprising an absorbent pad assembly having front and back waistline portions, a crotch portion intermediate the waistline portions, a lateral fold in the crotch region along a laterally extending fold line, and an elastic constraint across the location of the lateral fold line. In particular, one or more elastic strips 7, 8 have their opposite ends secured to the back surface 30 of a fluid-impervious backing sheet 28 of the diaper on opposite sides of fold line 80.

U.S. Pat. No. 4,023,571 issued May 17, 1977 to J. Comerford describes an absorbent nether garment liner which comprises an absorbent layer having a first and second major surface. The absorbent garment assumes a nonplanar arcuate shape.

U.S. Pat. No. 4,323,070 issued Apr. 6, 1982 to I. Ternstrom et al. describes a disposable diaper including a first outer layer of a liquid-permeable material intended to abut the body of the user, a second outer layer of a liquid-impermeable material and an intermediate layer of absorbent material arranged between the two outer layers. At least that portion of the diaper which is situated in the user's crotch is provided with elastic bands or threads extending between the two side edges of the diaper. These bands or threads are at least partially connected with pretension to the liquid-permeable outer layer.

U.S. Pat. No. 4,578,073 issued Mar. 25, 1986 to J. Dysart et al. describes a composite waste-containment garment comprising a disposable, elasticized waste-containment insert secured by means integral with the insert inside a nonelasticized over-garment. The insert comprises an absorbent core and a liquid-impervious backsheet.

Conventional absorbent article designs, such as those disclosed in the above documents, have not adequately addressed the problem of the migration of waste materials toward and past the waistband sections of the article. Conventional designs have also allowed excessive intermixing between any feces deposited in the rear portion of the article and urine deposited in the front portion of the article. In addition, the conventional absorbent article designs have not adequately addressed the problem of excessive folding or wrinkling of the bodyside liner material. Such folds and wrinkles may inhibit the rapid passage of fluids through the liner and into the absorbent pad. As a result, the conventional designs may experience excessive leakage of waste materials from the absorbent article. In conventional designs employing one or more large aperture openings through the bodyside liner material, there may be excessive contact between the wearer's skin and the wet absorbent pad. This can cause excessive hydration of the skin and discomfort to the wearer.

BRIEF DESCRIPTION OF THE INVENTION

The present invention provides a distinctive absorbent article, such as a disposable diaper, feminine care garment, incontinent garment or the like. Generally stated, the absorbent article comprises a backsheet layer, a substantially liquid-permeable liner layer, and an absorbent body located between the backsheet and liner layers.

The backsheet and liner layers generally define a front waistband section, a rear waistband section and an intermediate section of the article, with the intermediate section interconnecting the front and rear waistband sections. A resilient barrier section is located in the intermediate section of the article and includes at least a portion which extends generally transversely along the cross-direction of the article. The barrier member extends toward the body of the wearer and operably inhibits the longitudinal movement of liquid or viscous waste materials between the front and rear sections of the article. In a particular aspect of the invention, the resilient barrier section may comprise a linear or curvilinear ridge member composed of a foam or other compressible material which has sufficient, operable resiliency even when wet.

In another aspect of the invention, the resilient barrier member may comprise a plurality of longitudinally extending elastic members which are connected to the liner layer and are distributed in a substantially transversely and adjacently spaced relation over a medial portion of the intermediate section of the article. The elastic members have an active longitudinal extent of not more than about 50 percent of the total length of the absorbent article. The elastic members operably gather the liner layer to form therein a ruffled panel region which includes a plurality of transversely aligned ridges extending generally perpendicular from the liner layer and positioned at a predetermined portion of the absorbent article. The elastic members operably shorten the liner layer to reduce the occurrence of transversely aligned wrinkling and folding thereof at a designated region of the absorbent article.

The present invention can advantageously provide a system of one or more transverse ridges which extend over limited regions of the article's intermediate section to inhibit the movement of viscous waste materials, such as feces. In particular aspects of the invention, the system of ridges can help restrict the waste material to selected regions of the diaper and can reduce the mixing of liquid and solid wastes. The invention can also advantageously remove undesired folds from the liner layer at the insult target regions of the absorbent article. The reduction in the occurrence of folds can help enhance the penetration rate of fluid through the liner layer and into the absorbent body. As a result, the absorbent article provided by the present invention can help reduce leakage from the diaper and provide improved comfort to the wearer.

BRIEF DESCRIPTION OF THE DRAWINGS

The present invention will be more fully understood and further advantages will become apparent when reference is made to the following detailed description of the invention and the drawings, in which:

FIG. 2 representatively shows a top plan view of a diaper article of the present invention;

FIG. 2A representatively shows a top plan view of an alternative embodiment of the present invention;

DETAILED DESCRIPTION OF THE INVENTION

The following detailed description is made in the context of an absorbent article comprising a disposable diaper. It is readily apparent, however, that the present invention can be employed with other disposable articles, such as feminine care garments, incontinence garments and the like.

Figure 1:
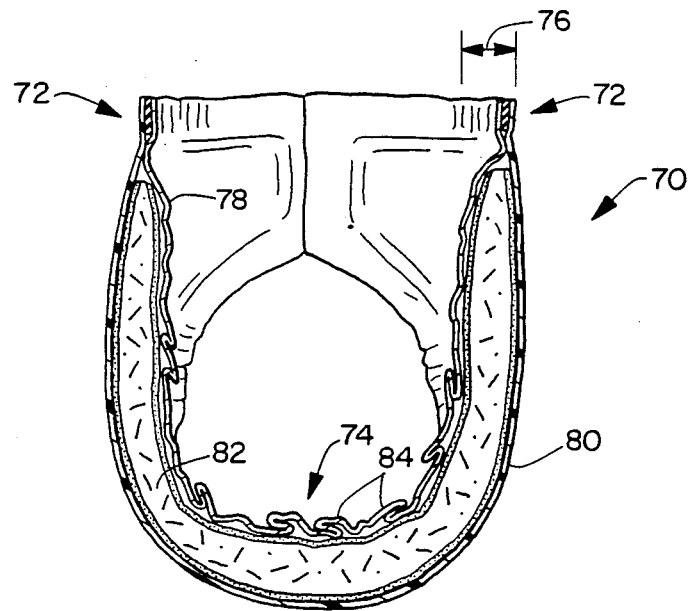
FIG. 1 representatively shows a cross-sectional, side view of a conventional diaper article which has been curved and bent for placement on a wearer.

With respect to FIG. 1, a conventional absorbent article, such as diaper 70, is typically manufactured in a substantially flat, planar configuration. The diaper generally comprises a liquid-impermeable outer cover 80, a liquid-permeable bodyside liner layer 78 and an absorbent pad 82 sandwiched between the outer cover and bodyside liner. The diaper delimits two waistband sections 72 and an intermediate section 74 which interconnects the waistband sections. The waistband sections are arranged to encircle the front and back portions of the wearer's waist, and the intermediate section is intended for placement in the crotch between the wearer's legs. The diaper has a significant thickness 76. As a result, when the diaper is curved along its longitudinal length for placement on the wearer, outer cover 80 follows an outer arc of circumference and constrains absorbent body 82 as the absorbent body curves and bends under the crotch of the wearer's body. Bodyside liner 78 wrinkles and folds to accommodate a relatively smaller arc of circumference which has a relatively shorter radius of curvature, as compared to outer cover 80. The wrinkles and folds 84 are substantially randomly located along the longitudinal length of the diaper. Typically, a folded section 84 of the bodyside liner produces a triple-layer of liner material. If the folds occur at the insult target region of the diaper, the multiple layers of liner material may undesirably reduce the penetration rate of fluid through bodyside liner 78 and into absorbent pad 82. Instead of penetrating directly into the absorbent pad, the fluid may spread laterally to other sections of the diaper, and in certain circumstances may become mixed with feces. As a result, the body wastes may excessively migrate toward the diaper edges and leak from the diaper. In addition, the mixed urine and feces tends to spread and contact more skin area. This could increase the amount of skin that may become irritated and increase the difficulty of cleaning the skin of the wearer.

To help prevent leakage, an improved absorbent article may be constructed in accordance with the present invention. As representatively shown in FIG. 2, an absorbent article, such as diaper 10, includes a backsheet layer 12, a substantially liquid-permeable liner layer 14, and an absorbent body 16 located between the backsheet and liner layers. The diaper, particularly the backsheet and liner layers, generally delimits a front waistband section 24, a rear waistband section 25, and an intermediate section 26 which interconnects the waistband sections.

A resilient barrier section 11 is located in intermediate section 26 and extends generally transversely along diaper cross-direction 64. Barrier section 11 has an upward extent (height) toward the body of the wearer, and is constructed and arranged to operably inhibit movement of liquid or viscous waste materials along diaper longitudinal direction 66. Such movement could undesirably allow a mixing of waste materials between the front and rear sections of the diaper.

In a particular aspect of the invention, the resilient barrier section 11 may comprise a linear or nonlinear ridge member 13 composed of a foam or other compressible material which is located on either the outward side or bodyside of liner 14 and has sufficient resiliency even when wet. In the embodiment representatively shown in FIG. 2, ridge member 13 extends along cross-direction 64 in a generally linear configuration. In the embodiment representatively shown in FIG. 2A, ridge member 13 extends along cross-direction 64 in a generally nonlinear configuration. More specifically, the ridge member illustrated in FIG. 2A may extend in a generally angular or curvilinear, U-shape configuration, with at least a portion of the ridge member arranged along the diaper cross-direction. In an alternative embodiment, the ridge member may extend in a generally H-shape configuration, with the upstanding "legs" of the "H" extending along the longitudinal dimension of the diaper and the "cross bar" extending along the diaper transverse dimension. By suitably angling or curving the layout of ridge member 13 to be substantially concave toward the rear and/or front waistband section of the diaper, the ridge member can inhibit the lateral, cross-directional movements of waste material as well as the longitudinal movements. As a result, the diaper can advantageously reduce sideways leakage of waste materials past the side margins of the diaper.

For the purposes of the present invention, the term "resilient" means a material of generally homogeneous or heterogeneous composition which is soft and deformable but springs back to approximately its original configuration after the deforming forces are reduced or removed. In a preferred aspect of the invention, the resilient material can spring back to at least about 50% of its original thickness (height) within 5 sec. after being compressed under a pressure of 120 g/cm$^2$. To provide improved performance, the resilient material can spring back to at least about 80% of its original thickness. The phrase "wet resilient" means a material which is "resilient" even when wetted or otherwise placed in intimate contact with water. Materials suitable for constructing ridge member 13 include, for example, spongy polymer foams, webs composed of woven or nonwoven fibers such as polyester fibers, or nonlinting mixtures of synthetic fibers and natural fibers such as woodpulp fibers.

Where ridge member 13 is composed of a resilient foam material, the bodyside surface of the foam material may optionally be slit, cut, grooved or otherwise relieved to thereby reduce the stiffness of the material and enable it to more readily conform to the body contours of the wearer. An example of a suitable polymer foam is an open cell, polyethylene foam, such as the LC-31 foam material distributed by Sentinel Foam, a company having offices in Hyannis, Mass.

Figure 3:
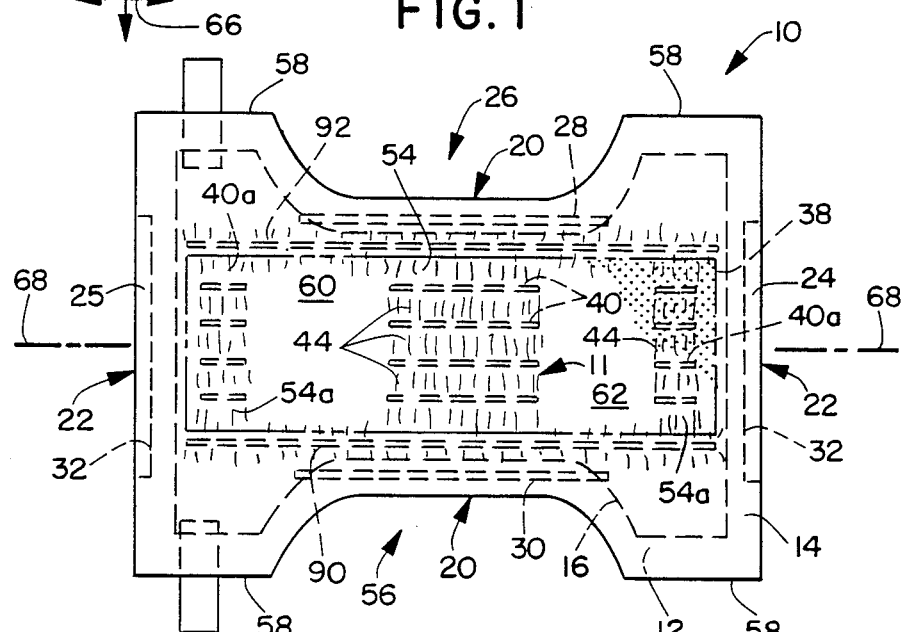
FIG. 3 representatively shows a top plan view of another aspect of the invention which includes a ruffled panel region.

In another aspect of the invention representatively shown in FIG. 3, resilient barrier section 11 may comprise a plurality of longitudinally extending elastic members 40 which are connected to liner layer and are transversely distributed in a substantially adjacently-spaced relation over a medial section 56 of the diaper. The elastic members are positioned in the intermediate, crotch section and have a longitudinal extent of not more than about 25 percent of the total length of diaper 10. Elastic members 40 operably gather liner layer 14 to form in the liner a ruffled panel region 54. The ruffled region includes a plurality of transversely aligned ridges 44 which extend generally perpendicularly away from the plane generally defined by liner layer 14, and are positioned at a limited, predetermined portion of diaper 10. Elastic members 40 can operably shorten liner layer 14 to reduce the occurrence of transversely aligned wrinkling and folding of the liner at a front insult target region 62 and a rear target region 60 of the diaper.

Typically, backsheet layer 12 and bodyside liner layer 14 extend past the terminal, marginal edges of absorbent body 16. As a result, flexible and gatherable side margins 20 are formed at the lateral sides of the diaper, and gatherable end margins 22 are formed at the longitudinal ends of diaper 10. Leg elastic members 28 and 30 are secured to the side margins of the diaper by suitable attaching means, such as adhesive, thermal bonding, sonic bonding and the like. Such attaching means may also be employed to assemble together the other component parts of the absorbent article. The leg elastics are arranged to operably gather and shir the side margins of the diaper to form stretchable, elasticized side flaps. When diaper 10 is placed on a wearer, the elasticized side flaps can form effective gasketing seals around the legs of the wearer. In addition, diaper 10 may include waist elastic members 32 secured to end margins 22 of the diaper. The waist elastics are secured to the end margins by suitable attaching means, and are arranged to operably form elasticized gathers in end margins 22. As a result, the elasticized end margins can form an effective gasketing seal around the wearer's waist.

The shown embodiment of diaper 10 has a generally I-shaped planform with laterally extending ears 58 located at the waistband sections of the diaper. At one waistband section of the diaper, suitable fastening means are secured to each of the associated ears. The fastening means may, for example, comprise adhesive tape tabs, Velcro-type fasteners, snaps, buttons, hook and loop type fasteners, or the like. Other embodiments of the invention can include, for example, a generally rectangular-shaped absorbent pad 16, and perforations formed through backsheet layer 12. In a particular embodiment of the invention, the perforations are formed through the side margins of backsheet 12. The perforations have diameters of up to about 0.20 inches and may be arranged to provide about 100–300 perforations per square inch of backsheet area. The perforated area preferably is limited to the portion of the side margins of the backsheet located between the terminal side edge of the backsheet and the innermost leg elastic member. If desired, however, the perforated area may cover a greater portion or a different selected region of the backsheet.

The various components of diaper 10 are assembled together employing conventional techniques. For example, the components may be attached to one another by employing thermal bonds, sonic bonds, or mechanical fasteners, such as snaps or clips. Alternatively, the components can be attached with adhesives, such as hot melt pressure-sensitive adhesives. The adhesives may be applied by employing conventional techniques, such as by spraying droplets or filaments of the adhesive. In the shown embodiment of the invention, the components are assembled employing a plurality of generally parallel lines of hot melt pressure-sensitive adhesive oriented along the length dimension of the diaper.

In a typical embodiment of the invention, backsheet 12 is composed of a liquid-impermeable material, such as a polymer film. For example, backsheet 12 can be composed of a polyolefin film, such as polyethylene or polypropylene. In another embodiment of the invention, backsheet 12 can be composed of a liquid-impermeable, but vapor-permeable material, such as a breathable, microporous polyethylene film. In yet another embodiment of the invention, the backsheet may be composed of a vapor-permeable, nonwoven fibrous material which has been suitably treated to import a desired degree of liquid impermeability. For example, backsheet 12 may comprise a nonwoven spunbonded layer which has been completely or partially coated with a polymer film to provide a sufficient level of liquid impermeability in selected regions of the backsheet.

Liner layer 14 is typically composed of a liquid-permeable, substantially hydrophobic fibrous material, such as a spunbonded web composed of synthetic polymer fibers. Alternatively, liner 14 may comprise a meltblown web or a bonded-carded web composed of synthetic polymer fibers. Suitable synthetic polymers include, for example, polyethylene, polypropylene and polyesters. In a particular aspect of the invention, the polymer filaments have a denier within the range of about 1.5–7, and preferably have a denier within the range of about 1.5–3. The filaments are arranged to form a nonwoven layer having a basis weight within the range of about 0.6–1.0 oz./sq. yd. In addition, the liner layer has a bulk thickness within the range of about 0.008–0.017 inch, and preferably has a bulk thickness within the range of about 0.010–0.012 inches for improved effectiveness. For the purposes of the present invention, the bulk thickness is measured under a restraining pressure of 0.014 psi. The liner layer has an effective pore size that readily allows the passage therethrough of liquids, such as urine. The liner layer can optionally be treated with surfactants to adjust its degree of hydrophobicity and wettability, and can also be selectively embossed or perforated with discrete slits or holes extending therethrough. When configured with perforations, the perforations may have an average effective diameter within the range of about 1600–3500 micrometers, and preferably have an average effective diameter of about 2500 micrometers to provide improved performance.

Absorbent body 16 typically comprises a pad composed of airlaid cellulosic fibers commonly referred to as wood pulp fluff. Conventional pads can have a density ranging from about 0.05–0.20 gm./cc., and are sufficiently flexible to readily conform to the body of the wearer. Absorbent body 16 may also comprise a coform material composed of a mixture of cellulosic fibers and synthetic polymer fibers. For example, the coform material may comprise an airlaid blend of cellulosic fibers and meltblown polyolefin fibers, such as polyethylene and polypropylene fibers. In one aspect of the invention, the fibrous material comprising absorbent body 16 is composed of filaments having a courseness within the range of about 10–20 milligrams per 100 meters, and preferably have a courseness within the range of about 10–18 milligrams per 100 meters. The filaments are arranged to form a layer having a basis weight within the range of about 400–1200 gm./meter$^2$ and preferably a basis weight of about 800 gm./meter$^2$.

Absorbent body 16 may also include an effective amount of an inorganic or organic high-absorbency material to enhance the absorptive capacity of the absorbent body. For example, absorbent body 16 can include 5–95 weight percent high-absorbency material, and preferably includes about 10–30 weight percent of the high-absorbency material to provide more efficient performance. Suitable inorganic high-absorbency materials include, for example, absorbent clays and silica gels. Organic high-absorbency materials can include natural materials, such as agar, pectin, guar gum, and peat moss, as well as synthetic materials, such as synthetic hydrogel polymers. Such hydrogel polymers include, for example, carboxymethylcellulose, alkyli metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyridine and the like. Other suitable polymers include hydrolized acrylonitrile grafted starch, acrylic acid grafted starch, and isobutylene maleic anhydride copolymers, and mixtures thereof. The hydrogel polymers are preferably lightly cross-linked to render the materials substantially water-insoluble. Cross-linking may, for example, be by irradiation or by covalent, ionic, Van der Waals, or hydrogen bonding. Suitable materials are available from various commerical vendors, such as Dow Chemical Company, Hoechst Celanese Corporation, Allied-Colloid, and Stockhausen. Typically, the high-absorbency material is capable of absorbing at least about 15 times its weight in water, and preferably is capable of absorbing at least about 25–50 times its weight in water.

The high-absorbency material can be distributed or otherwise incorporated into absorbent body 16 by employing various techniques. For example, the high-absorbency material can be substantially uniformly distributed in the mass of fibers comprising the absorbent body. The material can also be nonuniformly distributed among the fibers to form, for example, a generally continuous gradient, with either an increasing or decreasing concentration of high-absorbency material, as determined by observing the concentration moving from the body side of absorbent body 16 to the outer side of the absorbent body. Alternatively, the high-absorbency material can comprise one or more discrete layers or strips selectively segregated from the fibrous material of absorbent body 16.

Absorbent body 16 can optionally include a substantially hydrophilic tissue wrap 18 to help maintain the integrity of the air laid fibrous structure. The tissue wrap sheet typically comprises an absorbent cellulosic material, such as creped wadding or a high wet-strength tissue. In one aspect of the invention, wrap sheet 18 may be configured to provide a distinctive wicking layer which helps to rapidly distribute liquid into the mass of absorbent fibers comprising the absorbent body. More particularly, the wrap sheet material on one side of the absorbent fibrous mass can be bonded to the wrap sheet located on the opposite side of the fibrous mass. The bonds are positioned at discrete, separate regions and extend through the thickness of the fibrous mass. Such a configuration shapes the wrap sheet to form a plurality of individual funnels or quilts which help to direct liquids into the interior of the fibrous mass and provide a more rapid absorption of the liquid. An effective embodiment may further include a plurality of holes or apertures formed at least partially through the thickness of the fibrous mass, and may be configured such that the bonding of the oppositely-positioned layers of wrap sheet material occurs through these holes or apertures. The apertures limit the amount of intervening fibrous material and allow a more direct bonding between the wrap sheet layers. The bonding can comprise adhesive bonds, sonic bonds, thermal bonds or the like.

In accordance with the present invention, bodyside liner 14 may include one or more ruffled panel regions 54 and 54a, which are restricted to predetermined portions of the liner, as representatively shown in FIG. 3. Where a ruffled panel 54a is positioned at the waistband section of the diaper, the ruffled panel can help reduce leakage past the waistband edges of the diaper, and can help remove wrinkles and folds from the portion of the liner located at the intermediate section 26 of diaper 10. Where a ruffled panel 54 is located at the crotch section of diaper 10, the ruffled panel can help provide an isolation pocket at rear target zone 60 in the rear section of the diaper, or at fluid insult target zone 62 in the front section of the diaper. In particular, the ruffled panel in the crotch section of the diaper can help remove fold and wrinkles from the isolation pocket 60 and the insult target zone 62.

Ruffled panel sections 54, 54a include a plurality of generally longitudinally extending ruffle elastic members 40, 40a which are connected to liner layer 14 and are distributed over the cross-directional width dimension 64 of diaper 10. Elastic members 40, 40a are transversely spaced in a substantially adjacent relation over at least a medial section 56 (relative to the cross-dimension) of diaper 10. The elastic members may, for example, be connected to either the outward side or bodyside of the liner with suitable attaching means, such as adhesives, sonic bonds, thermal bonds and the like. The illustrated embodiment of the invention includes four elastic members 40, 40a in ruffled panels 54, 54a. A smaller or greater number of elastic members may also be incorporated into each ruffled panel. For example, the number of elastic members within each ruffled panel can be within the range of about 2–10.

In the shown embodiment, elastic members 40 are segregated from elastic members 40a and positioned in spaced, intermittent relation along a major portion of the diaper length. The total, cumulative extent of the elastic members, however, is not more than about 50 percent of the total length of diaper 10. Preferably, the total longitudinal extent of the ruffle elastics is within the range of about 5–30 percent of the total diaper length, and more preferably the total longitudinal extent is within the range of about 10–20 percent of the total diaper length to provide improved effectiveness. For the purposes of the present invention, the total diaper length is determined when the diaper is in its completely extended, ungathered condition. The extent of ruffle elastic members 40, 40a is determined when liner layer 14 is held in its completely extended, ungathered condition and the ruffle elastics are thereby held stretched.

Ruffle elastics 40, 40a are connected to liner layer 14 while the elastics are in a contractible condition. This may be accomplished, for example, by holding the ruffle elastics in a stretched, tensioned condition during the process of securing the elastics to liner 14. Alternatively, ruffle elastics 40, 40a may comprise an activatable elastic material which can be placed in a stretched, metastable state and then later activated by a suitable initiator to cause the elastic material to transform from its elongated metastable state to a stable, elastically contracted state. The activating mechanism may be, for example, heat, high energy radiation, particle beam radiation, a chemically reactive initiator, or the like.

If composed of an activatable material, the ruffle elastics (40, 40a) may be arranged to extend the full length of the diaper, but have only specific, limited portions activated to the elastically contractible state to produce the desired, segregated ruffled panels. With this configuration, the total length of the active, contractible portions of the elastic material would be less than about 50% of the total diaper length, as previously discussed. Similarly, the ruffle elastics may comprise an elastic material applied along the length of the diaper with selected, limited portions of the elastic deactivated to effectively eliminate the contractible property of the elastic material. The deactivated portions of the elastic material would correspond to those portions of the elastic which lie outside the predetermined ruffled panel regions. For example, some elastic materials can be "heat-killed" such that the heated portions of the elastic lose their elastic nature. Alternatively, selected lengths of the elastic material may be cut into a plurality of small segments to effectively deactivate the elastic nature of the material.

In a particular aspect of the invention, ruffle elastic members 40, 40a when assembled into the article, can be elongated at least about 100 percent relative to their contracted condition on liner 14. Preferably, the elastic members can be elongated about 100–800 percent, and more preferably can be elongated about 300–400 percent to provide improved effectiveness. Elastic members 40 should exhibit sufficient contracting force to form effective ridges within ruffled panel regions 54, but should not exhibit an excessive contracting force which produces undesired bunching of the diaper. In a further aspect of the invention, each of the several elastic members 40 provides a tension force of about 5–20 grams measured at 80 percent of the "full" elongation of the composite comprising liner 14 and elastic members 40. Preferably, the ruffle elastic member exhibits a tension force within the range of about 10–80 grams, and more preferably a tension force within the range of about 15–40 grams, as measured at the 80 percent elongation. The 80 percent elongation level is determined by completely extending to its ungathered condition the portion of liner 14 which contains the ruffle elastics being evaluated, and noting the resultant "fully" extended length of the ruffle elastics. The ruffle elastics are then allowed to retract to 80 percent of their "fully" extended length, and the tension forces exerted by the individual elastics are determined.

Within a ruffled panel region 54, 54a, ruffle elastic members 40, 40a operably produce a plurality of transversely aligned ridges 44 which extend transversely over the associated cross-directional, width dimension of absorbent body 16. In one aspect of the invention, ridges 44 extend about 50–100 percent of the absorbent width.

The cross-directional extent of ridges 44 can be varied, depending upon the location of the ridges and the particular type of wearer for which the diaper is designed. For example, the cross-directional extent of ridges 44 positioned at the rear waistband section of the diaper can have a smaller cross-directional extent than ridges positioned at the intermediate, crotch section of the diaper. The age of the intended wearer may also be a factor. For example, in a diaper designed for younger children who typically have softer stools, the ridges located in the crotch section of the diaper should preferably extend across the full cross-directional width of absorbent body 16. The ridges may even have a cross-directional extent which is greater than the width of the absorbent body. In a diaper designed for older children who typically have firmer stools, the cross-directional extent of the ridges may extend across the total width of the absorbent body, but may extend across less than the full width, if desired. In addition, ridges 44 cover a section of diaper 10 which measures at least about 2 cm. along the length dimension 66 of diaper 10 when the diaper is in its relaxed, gathered condition. Preferably, the diaper area having ridges 44 has a measurement within the range of about 3–20 cm., and more preferably has a measurement within the range of about 5–15 cm., as determined along the length dimension 66 of the diaper.

To provide an effective barrier against the movement of solid or semi-solid waste materials, ridges 44 have an average height dimension of at least about 0.2 cm., as measured from "peak to valley" of the ridges. Preferably, the average height of ridges 44 is within the range of about 0.3–1.2 cm., and more preferably is within the range of about 0.4–0.8 cm. to provide improved effectiveness.

Ridges 44 extend generally perpendicularly away from the surface generally defined by liner layer 14 and are positioned at the predetermined portions of diaper 10 generally defined by ruffled panel regions 54, 54a. It will be readily appreciated, however, that normal handling of the diaper may cause ridges 44 to flatten or otherwise distort to some extent, and may cause the ridges to extend at angles somewhat different than a precise perpendicular to liner layer 14. The barrier effect of ridges 44 can, however, be maintained even though there may be some variation in the particular geometry of the individual ridges 44. There is at least one ridge 44 in each ruffled panel 54, 54a. Preferably, each panel includes at least two ridges, and more preferably the number of ridges is within the range of about 2–10.

Ruffle elastic members 40 are arranged to operably shorten liner layer 14 to thereby reduce the occurrence of transversely aligned wrinkling and folding of the liner layer at predetermined, designated regions of the absorbent article. More particularly, ruffle elastics 40 can be configured to reduce the occurrence of wrinkles and folds at rear target 60 and at the front target region 62. When undesired folds and wrinkles are removed from target region 62, any liquid insult is presented with substantially a single layer of liner material. As a result, the liquid insult can more rapidly penetrate through liner 14 and into absorbent body 16. Where ruffle elastics 40 remove excessive wrinkles and folds from the liner material located at a rear portion of diaper 10, the elastic members can help produce a pocket which can more effectively contain solid or semi-solid waste materials. In addition, particular aspects of the invention, which include a ruffled panel 54 positioned in the crotch portion of diaper 10, can help reduce migration and mixing of liquid and solid waste materials.

As previously mentioned, the present invention contemplates an absorbent article having various arrangements of one or more ruffled panels. For example, diaper 10 may incorporate a ruffled panel 54a only in the front waistband portion of the diaper. In another embodiment, the diaper includes a ruffled panel 54a only in the rear waistband portion of the diaper, and in yet another embodiment, diaper 10 includes a ruffled panel 54 only at the intermediate, crotch portion of the diaper.

It is further contemplated that an absorbent article can include two or more ruffled panels 54, 54a. For example, diaper 10 may include a ruffled panel at the front waistband portion of the diaper and a ruffled panel at the rear waistband portion of the diaper. Another embodiment of diaper 10 includes a ruffled panel 54a at the diaper front waistband portion and a ruffled panel 54 at the diaper crotch section. Still another embodiment can include a ruffled panel 54a at the rear waistband portion of the diaper and a ruffled panel 54 at the crotch section of the diaper. In yet another embodiment of the invention, diaper 10 includes a ruffled panel at each of the front waistband, rear waistband, and intermediate sections of the diaper.

Figure 4:
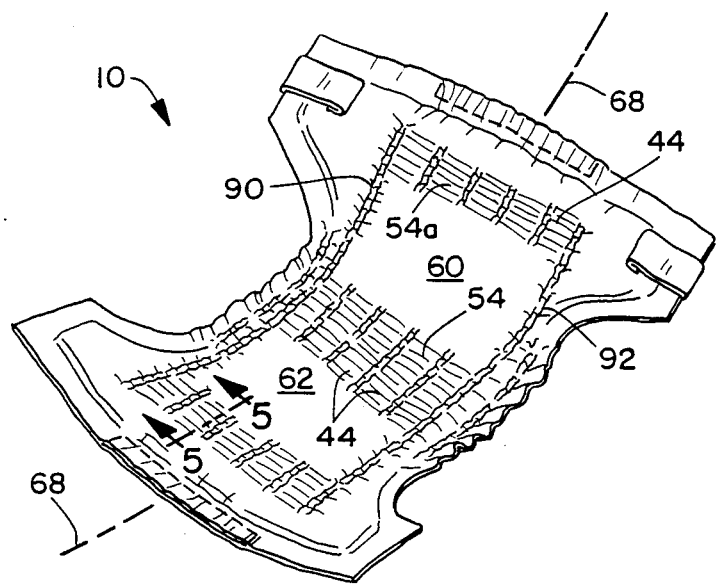
FIG. 4 representatively shows a perspective view of a diaper article wherein elastic members of restricted length have been employed to form barrier ridges which are generally aligned along the cross direction of the diaper in selected areas.
Figure 5:
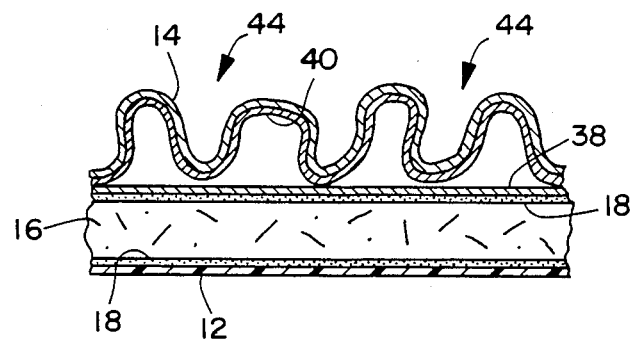
FIG. 5 representatively shows an enlarged cross-sectional view along line 5—5 of FIG. 4.
Figure 6:
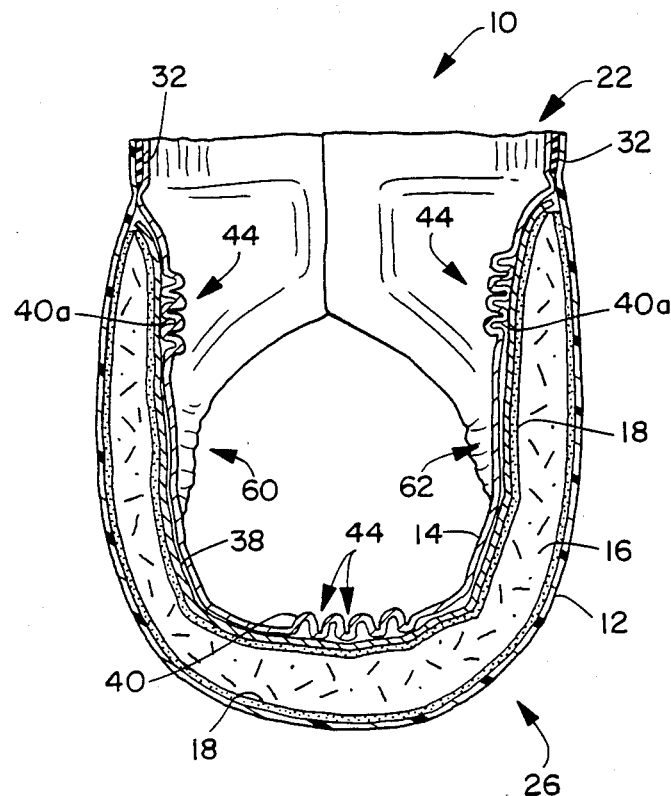
FIG. 6 representatively shows a cross-sectional, side view of a diaper article of the present invention which has been curved for placement on a wearer.

In a ruffled panel section 54a within a waistband section of the diaper, ruffle elastics 40a may extend up to about 25 percent of the total diaper length. Typically, the ruffle elastics are stretched to about four times its original, contracted length prior to assembly into the diaper. After the ruffle elastics have been assembled into the diaper and allowed to contract, as representatively shown in FIG. 4, the length of the gathered, ruffled panel region decreases to about one-third of its length when it is fully stretched and extended.

For example, in a typical medium-size diaper, the stretched length of ruffle elastics 40a at the diaper waistband sections may be about 2–5 cm. In addition, the stretched length of ruffle elastics 40 at the intermediate section of the diaper may be about 2–10 cm.

In one embodiment of a diaper particularly designed for use by children who have runny stools, the number of ruffled corrugations formed in the front waistband section could be reduced or omitted, and relatively more corrugations could be formed in the rear waistband section to reduce leakage from the back of the diaper. Similarly, in an embodiment designed primarily for use by older children who have firmer stools, the number of ruffled corrugations in the rear waistband section could be reduced, and relatively more corrugations could be formed at the front waistband section of the diaper. Such an arrangement would be particularly effective for reducing urine leakage from the front of diapers worn by children who sleep on their stomachs.

To help provide more effective containment at rear pocket region 60 and at front target region 62, diaper 10 may include a liner spacing means for resiliently urging selected lateral portions of liner layer 14 away from absorbent body 16 and toward a wearer's body. For example, in the illustrated embodiment, the spacing means comprises elastic spacing members 90, which are connected to the outwardly facing surface of liner 14. Optionally, the elastic members may be connected to the inwardly facing, bodyside surface of the liner. The elastic spacing members extend longitudinally along the length dimension 66 of diaper 10 and are attached to liner 14 while the elastic members are in an elongated, contractible condition. Spacing elastics 90 extend substantially continuously along at least about 40 percent of diaper length 66. In addition, spacing elastics 90 are positioned at a selected distance from the longitudinal centerline 68 of diaper 10. In a particular aspect of the invention, the cross-directional distance between elastic member 90 is within the range of about 7.6–13 cm. (about 3–5 in.), or about $\frac{1}{3}-\frac{2}{3}$ of the total diaper width at the intermediate, crotch region of the diaper. In the shown embodiment, the distance between spacing elastics 90 and 92 is within the range of about 10–13 cm.

In addition, spacing elastics 90 and 92 are spaced inboard from leg elastics 28 by a lateral distance which is within the range of about 1–4 cm. In another aspect of the invention, spacing elastics 90 and 92 are positioned to overlie absorbent body 16. The described configurations of spacing elastics 90 and 92 can advantageously provide a flexible, resilient barrier member positioned at each side of diaper centerline 68 to reduce side leakage of waste materials. Spacing elastic members 90 and 92 can operably draw liner layer 14 away from absorbent body 16 and toward the wearer's skin when the spacing elastics are allowed to contract and foreshortened the limited, lateral side sections of liner 14 to which the spacing elastics are attached. The drawing action produced by spacing elastics 90 and 92 help to provide a bowl-shaped configuration to rear pocket 60 and to front target region 62.

In an alternative embodiment of the invention, the liner portion of diaper 10 may include side containment pockets produced with elasticized containment flaps, which are formed integrally with or separately from the liner and configured to extend from the primary liner layer toward the wearer's body. The containment flaps are configured and arranged to extend along the longitudinal, length dimension of the diaper. Such containment flaps are representatively shown and described in U.S. Pat. No. 4,704,116 issued Nov. 3, 1987 to K. Enloe, which is hereby incorporated by reference to the extent it is consistent with the present specification. In a diaper or other absorbent article comprising the elasticized containment flaps, the cross-directional extent of ridges 44 can end at the location where the containment flaps connect or otherwise extend from the primary, layer structure of the liner.

To further improve the effectiveness of the absorbent article, diaper 10 may include a transport layer 38 which is interposed between liner 14 and absorbent body 16. Transport layer 38 can help provide an increased surge capacity during fluid insults, and provide a desired spacing between absorbent body 16 and liner layer 14. The spacing can help reduce the amount of wetness held against the wearer's skin. In a particular embodiment, transport layer 38 is connected to absorbent body 16 with a suitable fastening means, such as an adhesive. Alternatively, transport layer 38 may be connected to liner 14 to maintain a desired registry between the transport layer and the liner layer. For example, where liner layer 14 includes perforations therethrough, it may be desirable to insure that the perforated portions of liner 14 are maintained in registry over transport layer 38.

Transport layer 38 may be a nonwoven fibrous web composed of a substantially hydrophobic material, such as polypropylene, polyethylene, polyester or the like, and also may be composed of a blend of such fibrous materials. The transport layer is interposed between liner 14 and absorbent body 16 and is configured such that it is capable of attaining a substantially intimate contact with the liner and absorbent body. This intimate contact is useful for providing an effective fluid transfer communication from liner layer 14 to transport layer 38 and from transport layer 38 to absorbent body 16.

In the illustrated embodiment, transport layer 38 has a substantially uniform density, and has an essentially nonlayered configuration with the composition of the transport layer being substantially uniform throughout its structure. In a particular embodiment of the invention, transport layer 38 has a density within the range of about 0.015–0.5 gm./cc. Preferably, the transport layer has a density within the range of about 0.04–0.4 gm./cc., and more preferably has a density within the range of about 0.08–0.12 gm./cc. In addition, the fibers comprising transport layer 38 preferably have a denier within the range of about 1.5–15 to provide improved effectiveness. To adjust the performance of the invention, transport layer 38 may also be treated with a selected amount of surfactant to adjust its wettability. When treated with surfactants, however, the transport layer material should still be less hydrophilic than the material comprising absorbent body 16.

An example of a suitable transport layer material is a powder-bonded-carded web distributed by H. D. K. of Rogersville, Tenn. The web is composed of Kodel 435, 5.5 denier, polyester fibers bonded with Eastman 252 adhesive, which comprises about 16.6 weight percent of the web. The web has a bulk density of about 0.1 gm./cc., a bulk thickness of about 0.014 in., and a basis weight of about 30 gm./yd.$^2$. Another example of a suitable transport layer material is a spunbond web composed of polypropylene, trilobal fibers. The web has a bulk density of about 0.1 gm./cc., a bulk thickness of about 0.017 in., and a basis weight of about 35 gm./yd.$^2$. The spunbond web may also include about 0–0.5 weight percent of a surfactant, such as Triton X102 distributed by Rohm and Haas Company of Philadelphia, Penn. Further examples of suitable transport layer materials include spunbond webs composed of polypropylene fibers, which may be round, trilobal or poly-lobal in cross-sectional shape and which may be hollow or solid in structure. Such webs can have a basis weight within the range of about 0.5–2.0 oz./yd.$^2$, and a bulk thickness within the range of about 0.010–0.050 in. Typically, the webs are bonded, such as by thermal bonding, over about 3–30 percent of the web area.

Having thus described the invention in rather full detail, it will be readily appreciated that various changes or modifications may be made without departing from the spirit of the invention. All of such changes or modifications are contemplated as being within the scope of the present invention, as defined by the subjoined claims.

We claim:

1. An absorbent article, comprising:
   a backsheet layer;
   a substantially liquid-permeable liner layer;
   an absorbent body located between said backsheet and liner layers; and
   a plurality of longitudinally extending elastic members which are connected to said liner layer and transversely distributed in a substantially adjacently-spaced relation over a medial section of said article, said elastic members having a total, active longitudinal extent of not more than about 50 percent of the total length of said absorbent article, said elastic members operably gathering said liner layer to form therein one or more ruffled panel regions which include a plurality of transversely aligned ridges extending generally perpendicularly from said liner layer and positioned at a predetermined portion of said absorbent article, and said elastic members arranged to operably shorten said liner layer to reduce the occurrence of transversely aligned wrinkling and folding thereof at a designated region of said absorbent article.

2. An absorbent article as recited in claim 1, wherein said ruffled panel region is formed at a front waistband section of said article.

3. An absorbent article as recited in claim 1, wherein said ruffled panel region is formed at a rear waistband portion of said article.

4. An absorbent article as recited in claim 1, wherein said ruffled panel region is formed at an intermediate section of said article.

5. An absorbent article as recited in claim 1, wherein a first ruffled panel region is formed at a rear waistband section of said article and a second ruffled panel region is formed at an intermediate section of said article.

6. An absorbent article, comprising:
   a backsheet layer;
   a substantially liquid-permeable liner layer;

an absorbent body located between said backsheet and liner layers;

a plurality of longitudinally extending elastic members which are connected to said liner layer and transversely distributed in a substantially adjacently-spaced relation over a medial section of said article, said elastic members having a total, active longitudinal extent of not more than about 50 percent of the total length of said absorbent article, said elastic members operably gathering said liner layer to form therein one or more ruffled panel regions which include a plurality of transversely aligned ridges extending generally perpendicularly from said liner layer and positioned at a predetermined portion of said absorbent article, and said elastic members arranged to operably shorten said liner layer to reduce the occurrence of transversely aligned wrinkling and folding thereof at a designated region of said absorbent article; and resilient spacing means located at each side of a centerline of said article for urging lateral sections of said liner layer away from said absorbent body.

7. An absorbent article as recited in claim 6, wherein said ruffled panel region is located at a rear waistband section of said article.

8. An absorbent article as recited in claim 6, wherein a first ruffled panel region is located at a rear waistband section of said article and a second ruffled panel region is located at an intermediate section of said article.

9. An absorbent article as recited in claim 6, wherein said ruffled panel region in its ruffled condition extends over about 2-20 cm. of said absorbent article length.

10. An absorbent article as recited in claim 8, wherein said first ruffled panel region extends over about 2-5 cm. of said absorbent body length, and said second ruffled panel region extends over about 2-10 cm. of said absorbent article length.

11. An absorbent article as recited in claim 6, wherein said resilient spacing means comprises elastic spacing members which extend longitudinally along a length dimension of said article and are attached to said liner layer to contract and draw said lateral sections of said liner layer away from said absorbent body.

12. An absorbent article as recited in claim 6, wherein said resilient spacing means comprises elasticized containment flaps which are configured to extend longitudinally along a length dimension of said article.

13. An absorbent article, comprising:
a backsheet layer;
a substantially liquid-permeable liner layer;
an absorbent body located between said backsheet and liner layers, with one or more of said backsheet and liner layers extending beyond lateral side edges of said absorbent body to form gatherable side margins of said article;
one or more leg elastic members connected to each side margin to form elasticized gathers in the side margin;
a plurality of longitudinally extending elastic members which are connected to said liner layer and transversely distributed in a substantially adjacently-spaced relation over a medial section of said article, said elastic members having a total, active longitudinal extent of not more than about 50 percent of the total length of said absorbent article, said elastic members operably gathering said liner layer to form one or more ruffled panel regions which include a plurality of transversely aligned ridges extending generally perpendicularly from said liner layer and positioned at a predetermined portion of said absorbent article, and said elastic members arranged to operably shorten said liner layer to reduce the occurrence of transversely aligning wrinkling and folding thereof at a designated region of said absorbent article; and
resilient spacing means located at each side of a centerline of said article for urging lateral sections of said liner layer away from said absorbent body.

14. An absorbent article as recited in claim 13, wherein a first ruffled panel region is located at a rear waistband section of said article and a second ruffled panel region is located at an intermediate section of said article.

15. An absorbent article as recited in claim 13, wherein said resilient spacing means comprises elastic spacing members which extend longitudinally along a length dimension of said article and are attached to said liner layer to contract and draw said liner layer away from said absorbent body.

* * * * *